United States Patent
Saadi

(10) Patent No.: US 11,207,401 B1
(45) Date of Patent: *Dec. 28, 2021

(54) COVID-19 PEPTIDE SPECIFIC T-CELLS AND METHODS OF TREATING AND PREVENTING COVID-19

(71) Applicant: Tevogen Bio Inc., Metuchen, NJ (US)

(72) Inventor: Ryan Saadi, Metuchen, NJ (US)

(73) Assignee: Tevogen Bio Inc., Metuchen, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/314,154

(22) Filed: May 7, 2021

Related U.S. Application Data

(62) Division of application No. 17/116,227, filed on Dec. 9, 2020.

(51) Int. Cl.
*A61K 39/215* (2006.01)
*C12N 5/0784* (2010.01)
*A61K 9/00* (2006.01)
*C12N 5/0783* (2010.01)

(52) U.S. Cl.
CPC .......... *A61K 39/215* (2013.01); *A61K 9/0019* (2013.01); *C12N 5/0638* (2013.01); *C12N 5/0639* (2013.01); *C12N 2502/1192* (2013.01); *C12N 2506/115* (2013.01)

(58) Field of Classification Search
None
See application file for complete search history.

(56) References Cited

U.S. PATENT DOCUMENTS

| | | | |
|---|---|---|---|
| 9,963,677 B2 | 5/2018 | Leen et al. | |
| 2008/0056994 A1* | 3/2008 | Kaneski | A61K 31/45 424/9.2 |
| 2017/0319683 A1* | 11/2017 | O'Reilly | A61P 11/00 |

OTHER PUBLICATIONS

Ferretti et al. (Immunity. Nov. 17, 2020; 53: 1095-1107).*
Leung et al. (Advances in Cell and Gene Therapy. Published Jul. 12, 2020; 3: e101).*
Zhao et al. (Journal of Virology, Sep. 2010; 84 (18): 9318-9325).*
U.S. Appl. No. 17/116,227, Tevogen Bio Inc., filed Dec. 9, 2020.
U.S. Appl. No. 17/314,152, Tevogen Bio Inc., filed May 7, 2021.
Zhao, J. et al., "T Cell Responses are Required for Protection from Clinical Disease and for Virus Clearance in Severe Acute Respiratory Syndrome Coronavirus-Infected Mice," J. of Virology, 84(18):9318-9325 (2010).
Yu et al., Sequence alignment of instant SEQ 29 with Geneseq db access No. BID47971, Oct. 2020.
Yu et al., Sequence alignment of instant SEQ 44 with Geneseq db access No. BID47971, Oct. 2020.
Chen, Y. et al., "Aging in Covid-19: Vulnerability, immunity and intervention," Ageing Research Review 65 (101205):1-11 (2021).
Leung, W. et al., "Rapid production of clinical-grade SARS-CoV-2 specific T cells," Advances in Cell and Gene Therapy, 3(4):1-8 (2020).
Naik, S. et al.,"Adoptive Immunotherapy for Primary Immunodeficiency Disorders with Virus-specific T Lymphocytes," J. of Allergy and Clinical Immunology, 137(5): 1498-1505 (2016).
Oh, H. et al., "Engineering T Cells Specific for a Dominant Severe Acute Respiratory Syndrome Coronavirus CD8 T Cell Epitope," J. of Virology, 85(20): 10464-10471 (2011).
Ferreras, C. et al., "SARS-CoV-2-Specific Memory T Lymphocytes from COVID-19 Convalescent Donors: Identification, Biobanking, and Large-Scale Production for Adoptive Cell Therapy," Frontiers in Cell and Developmental Biology, 9:1-12 (2021).
Liu, K., "Dendritic Cells," Encyclopedia of Cell Biology, 3:741-749 (2016).
Gigante, M. et al., "In Vitro\Ex Vivo Generation of Cytotoxic T Lymphocytes," Methods in Molecular Biology, 1186:13-20 (2014).
Tregoning, J. et al., "Progress of the COVID-19 vaccine effort: viruses, vaccines and variants versus efficacy, effectiveness and escape", Nature Reviews Immunology, 21: 626-636 (2021).
Sivapalan, R. et al., "Virus Induced Lymphocytes (VIL) as a novel viral antigen-specific T cell therapy for COVID-19 and potential future pandemics," Nature Scientific Reports, 11:15295 (2021) https://doi.org/10.1038/s41598-021-94654-y.
Kleiveland, Charlotte R. "Peripheral Blood Mononuclear Cells" in The Impact of Food Bio-Actives on Gut Health (Kitty Verhoeckx ed., Springer Open 2015), Chapter 15, pp. 161-167.
Sharma, et al., "Leukoreduced blood components: Advantages and strategies for its implementation in developing countries," Asian J. Transf Sci. 4(1):3-8 (2010).
Mathew J. et al., "Physiology, Blood Plasma" in: StatPearls, StatPearls Publishing LLC [retrieved from the Internet on Oct. 12, 2021], https://www.ncbi.nlm.nih.gov/books/NBK531504/ (2021).

* cited by examiner

*Primary Examiner* — Shanon A. Foley
(74) *Attorney, Agent, or Firm* — Hogan Lovells US LLP

(57) ABSTRACT

The invention relates to pharmaceutical compositions that contain COVID-19 peptide specific cytotoxic T cells, and to methods for treating or preventing COVID-19 infection.

11 Claims, 1 Drawing Sheet

Specification includes a Sequence Listing.

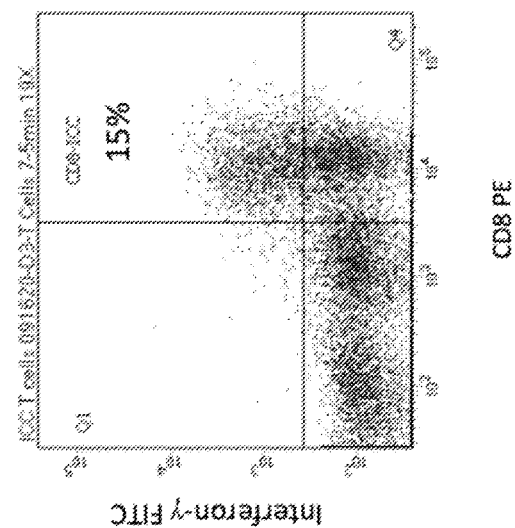
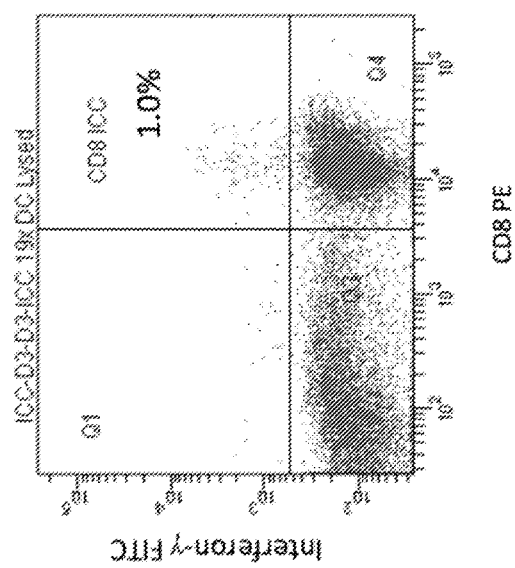
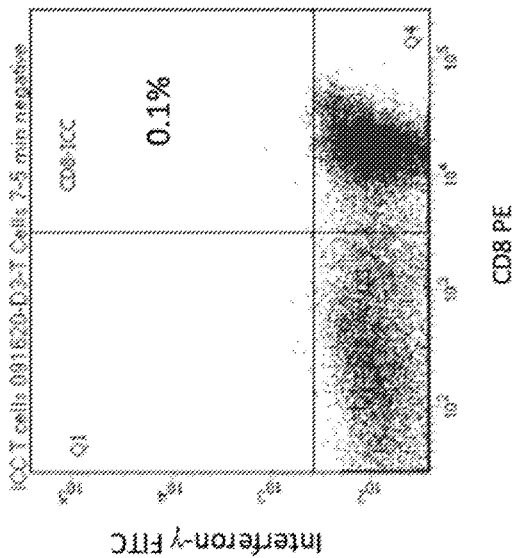

US 11,207,401 B1

COVID-19 PEPTIDE SPECIFIC T-CELLS AND METHODS OF TREATING AND PREVENTING COVID-19

RELATED APPLICATIONS

This application is a division of U.S. patent application Ser. No. 17/116,227, filed on Dec. 9, 2020, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Feb. 4, 2021, is named 767095_000013_SL.txt and is 14,179 bytes in size.

BACKGROUND OF THE INVENTION

Severe acute respiratory syndrome coronavirus 2 (SARS-CoV-2, commonly known as COVID-19) is a novel enveloped betacoronavirus closely related to two bat-derived severe acute respiratory syndrome (SARS)-like coronaviruses. (Lu et al., 2020) Infection with COVID-19 was first described in China in December of 2019, but in the ensuing months became a worldwide pandemic. In the United States, the first case of COVID-19 was reported in January of 2020, and as of August, 2020, there were 5,821,819 cases and 179,708 deaths. (Johns Hopkins Coronavirus Resource Center, 2020) While progress has been made in developing algorithms to treat the infection in the most seriously affected patients, (Recovery Collaborative Group, 06/22/2020) COVID-19-related mortality continues to be a significant problem especially in specific vulnerable populations. Elderly and immune compromised individuals, those with comorbidities such as diabetes or cardiovascular disease, and minorities have higher rates of death from COVID-19 infection (Guan et al., 2020; Stokes et al., 2020) as compared to the rest of the population. Although the status of vaccine trials and pending approvals is changing rapidly, at the time of filing this application vaccination of the majority of the population is still a longs ways off. In addition, questions remain about the durability of immunity after COVID-19 infection and vaccination. (To et al., 2020) With the coming Fall/Winter 2020 season approaching and as COVID-19 restrictions ease to counterbalance the catastrophic effects of the pandemic on mental health, (Pfefferbaum & North, 2020) non-COVID-19 health care, (Rosenbaum, 2020) and the economy, (Ip, 2020) COVID-19 infections will continue to occur or potentially increase in frequency.

Therefore, additional treatments are urgently needed for the treatment of acutely ill patients. There are currently no SARS-CoV-2 therapeutics or prophylactics available, and although clinical testing for a vaccine has begun, it will be at least several months before a vaccine would be ready for the public if successful. Thus, a desperate need exists for an effective therapeutic agent for treating and preventing COVID-19 in the future.

SUMMARY OF THE INVENTION

This disclosure relates to methods for treating COVID-19, including SARS-CoV-2 induced severe acute respiratory distress syndrome. The methods of this disclosure involve administering an effective amount of COVID-19 peptide specific T-cells to a subject in need thereof.

Aspects of the invention relate, in some embodiments, to a method of treating COVID-19 infection, comprising administering to a patient in need thereof an effective amount of COVID-19 peptide specific cytotoxic T lymphocytes (CTLs). In some embodiments, the patient is an elderly or immunocompromised patient. In some embodiments, administering is done by intravenous infusion. In some embodiments, the infusion is delivered to the patient through a central line or midline. The COVID-19 peptide specific CTLs can be from a single donor. In some embodiments, the COVID-19 peptide specific CTLs were sensitized against one or more peptides restricted against an HLA-A1 allele. In some embodiments the peptides are selected from the list consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, or a combination thereof. In some embodiments, the COVID-19 peptide specific CTLs were sensitized against one or more peptides restricted against an HLA-A2 allele. In some embodiments, the one or more peptides are selected from the list consisting of SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, or a combination thereof. In some embodiments, the COVID-19 peptide specific CTLs were sensitized against one or more peptides restricted against an HLA-B7 allele. In some embodiments, the one or more peptides are selected from the list consisting of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, or a combination thereof. In some embodiments, the COVID-19 peptide specific CTLs were sensitized against one or more peptides restricted against an HLA-B40 allele. In some embodiments, the one or more peptides selected from the list consisting of SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, or a combination thereof. In some embodiments, the COVID-19 peptide specific CTLs were sensitized against one or more peptides restricted against an HLA-Cw7 allele. In some embodiments, the one or more peptides are selected from the list consisting of SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77. In some embodiments, the COVID-19 peptide specific CTLs were sensitized against a combination of COVID-19 peptides binding to any one or combination of HLA-A1, A2, B7, B40, Cw7 alleles.

Other aspects involve preparing COVID-19 peptide specific cytotoxic T cells (CTLs) comprising the steps of: obtaining dendritic cells; pulsing the dendritic cells with a limited number of COVID-19 peptides known to bind to a HLA restriction element; obtaining lymphocytes; stimulating the lymphocytes with the peptide pulsed dendritic cells; co-culturing the dendritic cells and the lymphocytes for at least 6 days to form a monocyte monolayer; enriching T cells of the monocyte monolayer during a second stimulation process with the COVID-19 peptides; selecting the T cells by incubating the monocytes and activated lymphocytes for about 5 to 10 minutes; and expanding the T cells. In some embodiments at least 20% viral reactive CTLs are produced.

Other aspects involve pharmaceutical compositions comprising COVID-19 peptide specific cytotoxic T cells (CTLs). In some embodiments the CTLs are from multiple donors. In some embodiments the CTLs may be restricted by two or more different HLA-alleles.

BRIEF DESCRIPTION OF THE DRAWINGS

FIG. 1 is a panel of graphs showing the expansion of COVID-19 CTLs through the application of proposed laboratory processes. The left panel shows the background level, the center panel is after one week of in vitro culture, and the right panel illustrates enrichment to 15% after selection and further expansion after about three to four weeks of in vitro culture.

DETAILED DESCRIPTION

Applicant has developed methods for treating COVID-19 infected patients by administering novel preparations of COVID-19 peptide-specific cytotoxic T lymphocyte (CTL) products that can be used for immunological treatment in patients who are seriously ill with a COVID-19 infection. The role of T cells in eradicating viral infections and the adverse prognostic impact of lymphopenia in COVID-19 infection provides the scientific and clinical rationale for this effort.

The compositions and methods described herein can be used to focus the response on diverse targets, thereby providing a safety net that precludes the COVID-19 virus escaping from mutation. For example, all of the vaccines currently being developed target the S protein. If a viral mutation develops in the S protein, then the response may be compromised. Existing therapeutic and prophylactic therapies are not rationally designed and generally include a mix of CD4 and CD8, thereby making it difficult, if not impossible to identify the specific parts of the viral genome evoking the response. In contrast, the present invention allows one of skill in the art to know what we're immunizing with and what part of the viral genome it comes from. Thus, it is possible to assess the response to each peptide separately within the overall mixture and attach the virus diversely. As a result of the diversity included in the present invention, the COVID-19 virus is less likely to escape than if the only focus is on the S protein. Described herein are methods of treating COVID-19 infected patients with novel COVID-19 peptide-specific CTLs. Infected patients receive an infusion of COVID-19 peptide-specific CTLs manufactured using a three step (optionally, four step) process comprising in vitro stimulation-expansion cycles to produce the final CTL products described herein.

Definitions

The term "pharmaceutical composition" as used herein refers to a formulation that contains an effective amount of COVID-19 peptide specific cytotoxic T lymphocytes (CTLs).

As used herein, the terms "administration" or "administering" of COVID-19 peptide specific T cells refers to introducing CTLs to the blood of a patient through an intravenous infusion.

The term "effective amount," as used herein, refers to the amount of agent needed to achieve the desired effect. The actual effective amount for a particular use can vary according to the mode of administration, and the age, weight, general health of the subject, and severity of the symptoms or condition being treated. Suitable amounts of COVID-19 peptide specific CTLs to be administered, and dosage schedules, for a particular patient can be determined by a clinician of ordinary skill based on these and other considerations.

The term "pharmaceutically acceptable excipient" as used herein means that the excipient can be administered with no significant adverse toxicological effects on the respiratory tract. Such excipients are generally regarded as safe (GRAS) by the U.S. Food and Drug Administration.

The term "COVID-19-like illness" as used herein refers to illness that presents COVID-19-like symptoms, defined by the US Centers for Disease Control as fever, cough, and/or shortness of breath. COVID-19-like illness does not include COVID-19.

Methods of Treatment, Prophylaxis, and Reducing Contagion

In one aspect, the invention relates to methods for treatment, prophylaxis and for reducing contagion of COVID-19. The methods involve administering, by intravenous infusion, an effective amount of COVID-19 peptide specific T cells to a subject in need thereof. The peptide specific T cells may be administered by intravenous delivery to the subject, for example, by administration through a central line, midline, or peripheral IV.

In some embodiments, prior to administration of the COVID-19 peptide specific CTLs, patients will undergo full HLA typing and then be treated with an appropriate CTL.

In one embodiment, prior to administration of the COVID-19 peptide specific CTLs, patients will have their blood tested for rapid, low resolution human leukocyte antigens (HLA) typing with high resolution PCR SSP supplementation to determine if they have a potentially appropriate HLA antigen for the treatment (HLA-A1, A2, B7, B40, Cw7). The high-resolution supplementation will ensure that they are HLA-A*01:01, A*02:01, B*07:02, B*40:01, C*07:02 and thus match the CTL for one or more alleles.

Prior to administration of the COVID-19 peptide specific CTLs, pre-medications may be administered. In some embodiments, patients may receive pre-medications, such as diphenhydramine and acetaminophen. The diphenhydramine dose may be about 15, 20, 25, or 30 mg. The acetaminophen dose may be about 500, 550, 600, 650, 700, or 750 mg.

Patients may also be treated with remdemsivir or other standard of care pharmaceutical formulations prior to, concurrently with, or subsequently to administration of the COVID-19 peptide specific CTLs.

An effective dose of COVID-19 peptide specific CTLs is based on body weight and may be between $1 \times 10^5$ total cells/kg and $3 \times 10^6$ total cells/kg. A dose of $1 \times 10^5$ total cells/kg, $2 \times 10^5$ total cells/kg, $3 \times 10^5$ total cells/kg, $4 \times 10^5$ total cells/kg, $5 \times 10^5$ total cells/kg, $6 \times 10^5$ total cells/kg, $7 \times 10^5$ total cells/kg, $8 \times 10^5$ total cells/kg, $9 \times 10^5$ total cells/kg, $1 \times 10^6$ total cells/kg, $2 \times 10^6$ total cells/kg, $3 \times 10^6$ total cells/kg, $4 \times 10^6$ total cells/kg, $5 \times 10^6$ total cells/kg, $6 \times 10^6$ total cells/kg, $7 \times 10^6$ total cells/kg, $8 \times 10^6$ total cells/kg, or $9 \times 10^6$ total cells/kg may be administered. In some embodiments the dose will be measured by the number of COVID reactive cells instead of the total amount. For example, an effective dose may be between $1 \times 10^5$ COVID reactive cells cells/kg and $3 \times 10^6$ total cells COVID reactive cells/kg. A dose of $1\times10^5$ COVID reactive cells/kg, $2\times10^5$ COVID reactive cells/kg, $3\times10^5$ total cell COVID reactive cells s/kg, $4\times10^5$ COVID reactive cells/kg, $5\times10^5$ COVID reactive cells/kg, $6\times10^5$ COVID reactive cells/kg, $7\times10^5$ COVID reactive cells/kg, $8\times10^5$ COVID reactive cells/kg, $9\times10^5$ COVID reactive cells/kg, $1\times10^6$ total cells COVID reactive cells/kg, $2\times10^6$ COVID reactive cells/kg, $3\times10^6$ COVID reactive cells/kg, $4\times10^6$ COVID reactive cells/kg, $5\times10^6$ COVID reactive cells/kg, $6\times10^6$ COVID reactive cells/kg, $7\times10^6$ COVID reactive cells/kg, $8\times10^6$ COVID reactive cells/kg, or $9\times10^6$ COVID reactive cells/kg may be administered In some embodiments the effective dose will be based on actual body weight. In certain embodiments, where the actual weight is higher than the ideal weight, the dose will be based on adjusted body weight (ideal body weight+ 40% the difference between actual and ideal weight). Ideal weight for height is calculated from the formula of BJ Devine (1974): Male: 50.0 kg+2.3 kg per inch over 5 feet and Female: 45.5 kg+2.3 kg per inch over 5 feet.

An "effective amount" of pharmaceutical compositions comprising COVID-19 peptide specific CTLs is administered to an individual in need thereof, such as an individual who has COVID-19, has an COVID-19-like illness, is experiencing COVID-19-like symptoms or who is at risk for infection by COVID-19 virus. An effective amount is an amount that is sufficient to achieve the desired therapeutic or prophylactic effect, such as an amount sufficient to reduce COVID-19, COVID-19-like illness or COVID-19-like symptoms, to reduce duration of illness, to reduce COVID-19 virus titer in an individual, to reduce the number of days that infected individuals experience COVID-19-like symptoms and/or require oxygen by any means, to reduce the number of patients who develop COVID-19 related cytokine release syndrome, and/or to decrease the incidence or rate of COVID-19 virus infection. A clinician of ordinary skill can determine appropriate dosage and optionally, anti-COVID-19 agent, based on, for example, the individual's age, sensitivity, tolerance and overall well-being. The COVID-19 peptide specific CTLs can be administered in a single dose or multiple doses as indicated.

Intravenous delivery of the CTLs (e.g., infusion through a peripheral line, central line or midline) should take less than 10 minutes. In some embodiments the time to infuse the CTLs is about 10 minutes, about 9 minutes, about 8 minutes, about 7 minutes, about 6 minutes, about 5 minutes, about 4 minutes, about 3 minutes, about 2 minutes, or about 1 minute.

In one embodiment, the method comprises administering an effective amount of a pharmaceutical composition to an individual suspected of having COVID-19, with confirmed COVID-19 or at risk for COVID-19 (e.g., at risk for infection by coronavirus). The methods also comprise administering an effective amount of a pharmaceutical composition to an individual with COVID-19-like illness.

The pharmaceutical compositions are intended for administration to the blood of a patient, and can be administered in any suitable form, such as intravenously.

In some aspects, the therapeutic method comprises administering to an individual suspected of having COVID-19 or at risk of having COVID-19 an effective amount of a pharmaceutical composition of the invention. For example, in some embodiments the individual is suspected of having COVID-19 and has one or more symptoms of COVID-19. Symptoms of COVID-19 are well-known and include fever, cough, and shortness of breath. Additional symptoms of COVID-19 include difficulty breathing, persistent pain or pressure in the chest, confusion, inability to arouse, bluish lips or face.

In some embodiments, the method is for treating COVID-19 infection, and comprises administering to an individual in need thereof an effective amount of a pharmaceutical composition of the invention. In other embodiments, the method is for the prophylaxis of COVID-19 infection and comprises administering to an individual at risk for infection by COVID-19 virus an effective amount of a pharmaceutical composition of the invention. In other embodiments, the method is for reducing the spread of COVID-19 infection comprising administering to an individual infected by COVID-19 virus or at risk for infection by COVID-19 virus an effective amount of a pharmaceutical composition of the invention.

Suitable intervals between doses that provide the desired therapeutic effect can be determined based on the severity of the condition (e.g., infection), overall well-being of the subject and the subject's tolerance to the pharmaceutical compositions, and other considerations. Based on these and other considerations, a clinician can determine appropriate intervals between doses. Generally, a pharmaceutical composition is administered once, but may be administered every one to four days, or once a week, as needed.

The therapeutic methods and uses of the invention provide particular benefits when the individual suspected of having COVID-19, with confirmed COVID-19, at risk for COVID-19 (e.g., adults over 60 years, those with serious chronic medical conditions (such as heart disease, diabetes, lung disease), immunocompromised individuals), patients with recent cancer treatment, or with COVID-19-like illness also has a pulmonary disease, such as asthma (e.g., allergic/atopic, childhood, late-onset, cough-variant, or chronic obstructive), airway hyperresponsiveness, allergic rhinitis (seasonal or non-seasonal), bronchiectasis, chronic bronchitis, emphysema, chronic obstructive pulmonary disease, cystic fibrosis, early life wheezing, and the like. These patient populations are particularly susceptible to COVID-19 and other respiratory infections, and these infections are frequent causes of acute exacerbation of the underlying pulmonary disease. Accordingly, the methods and therapeutic uses described herein can provide additional benefit in these patient populations by reducing the incidence, duration and/or severity of acute exacerbations of the underlying pulmonary disease.

After administration, successful treatment will be determined by testing patient blood and/or nasal or nasopharyngeal swab specimens for viral diagnostics, CTL persistence, the formation of endogenous CTL and antibody responses to COVID-19. Responses to treatment may be tested, for example, at 4 days, 7 days, 14 days, 28 days, 2 months, 3 months, and 6 months post-infusion.

Methods for Preparing COVID-19 Peptide Specific CTLs

The COVID-19 peptide specific CTLs used in the methods of treatment provided herein can be prepared using any suitable method, for example allogeneic mononuclear leukocytes can be collected from a donor using standard leukapheresis techniques and then sensitized with COVID-19 peptides. The lymphocytes can be exposed to a limited number of peptides known to bind to the HLA restriction element of interest. For example, lymphocytes may be stimulated with 1, 2, 3, 4, 5, 6, 7, 8, 9, 10, 11, 12, 13, 14, 15, 16, 17, 18, 19, 20, 1 to 5, 1 to 10, 1 to 15, 1 to 20, 2 to 5, 2 to 10, 2 to 15, 2 to 20, 5 to 10, 5 to 15, 5 to 20, 10 to 20, or 15 to 20 peptides known to bind to the HLA restriction element of interest. The COVID-19 specific CTLs may be derived from peripheral blood lymphocytes.

The specific peptides used in this method will change over time as new peptides are discovered, and existing peptides are demonstrated not to work well during testing. The list of peptides provided in this application is not exhaustive, and will continue to evolve as a dynamic list.

In one aspect, lymphocytes undergo three in vitro stimulation-expansion cycles to produce the final CTL products used in the methods of treatment described herein. Each of these three stimulation-expansion cycles has a different purpose within the overall production process, and each therefore follows a distinct procedure. Optionally, a fourth restimulation may be performed. The fourth restimulation may be performed (1) for products which fall slightly short of meeting release criteria when it is anticipated that an additional round of stimulation and expansion will allow the product to meet these criteria or (2) if additional cell expansion is desired and it is thought that an additional round of stimulation and expansion will likely significantly increase the number of treatment doses which can be obtained from that batch. Any such optional fourth restimulation may be performed following the identical process for the third stimulation.

In one embodiment, mononuclear cells from healthy volunteer donors are separated by elutriation into lymphocyte and monocyte fractions. Lymphocytes are stimulated with peptides derived from the known sequence of the viral genome and predicted/demonstrated to bind to specific HLA alleles. Viral derived products are not utilized. In the first stimulation, a subset of the collected monocytes are treated so as to induce their maturation into dendritic cells. Dendritic cells are pulsed with one or more COVID-19-specific peptides and co-cultured with lymphocytes for 7 days. The second and third stimulations utilize monocytes to present the peptides and again allow 7-12 days for stimulated lymphocytes to grow/expand. The second stimulation also includes an enrichment step which helps to select for peptide specific CTLs (due to preferential adherence of T cells recognizing the pulse peptides to an adherent monocyte layer) and reduces the content of other non-specific 'bystander' lymphocytes or other immune cells from the donor. The third stimulation again uses monocytes and peptides, but does not repeat this selection step.

Most of the procedures described herein are performed in RPMI-1640 with 10% heat inactivated AB serum. The amount of AB serum in the media may be reduced to 9%, 8%, 7%, 6%, 5%, 4%, 3%, 2%, or 1%. Serum-free media and autologous plasma may be used as alternatives. This is referred to as "complete media" or CM. Any suitable media may be used, as determined by one of skill in the art, such as AIM V or other serum free media preparations alone, with 10% or lower concentrations of pooled serum or autologous serum or plasma, RPMI-1640 with serum substitutes with or without lower concentrations of pooled serum or autologous serum or plasma.

In a particular embodiment, the first stimulation, referred to as the Initial In Vitro Sensitization, lymphocytes are stimulated with peptides for a given HLA allele as a pool, not as individual peptides. An initial list of peptides for the five HLA alleles are included in the Examples below. The list of suitable peptides is expected to expand as new information continues to become available during the pandemic, and one of ordinary skill in the art will be able to identify additional peptides for use in the methods described herein. It is also possible that some peptides from the initial list will be removed.

For the initial in vitro sensitization, dendritic cells are used as antigen presenting cells. These cells are prepared from elutriated monocytes. Fresh or freshly thawed monocytes can be enriched by adherence to plastic. A suitable number of monocytes are resuspended in media and then cells are transferred to a tissue culture plate. The cells are then incubated for a suitable time (e.g., at least 60 minutes, at least 90 minutes, at least 120 minutes) to allow the monocytes to adhere to the culture plate. After incubation, the supernatant is removed from the culture plate. Adherent cells may then then be cultured with GM-CSF and IL-4 for a suitable time (e.g., 24 hours), at which point maturation cytokines (e.g., TNF-alpha, IL-1 beta, IL-6, and/or prostaglandin E2) may be added. After another 24 hours of culture, the dendritic cells detach and are ready for harvest by aspiration and centrifugation of the media. The duration of culture in maturation cytokines may, if necessary, be extended beyond 24 hours to about 30 hours, about 36 hours, about 42 hours, or up to about 48 hours.

Following their harvest, dendritic cells are pulsed with peptides (e.g., 2 microgram/ml each) for a suitable length of time (e.g., for about 60, 75, 90, or 120 minutes) and co-cultured thereafter with lymphocytes in tissue culture flasks (e.g., 75 cm$^2$) in media (e.g., CM). The ratio of lymphocytes to dendritic cells in culture may be 15:1, 16:1, 17:1, 18:1, 19:1, 20:1, 21:1, 22:1, 23:1, 24:1, or 25:1. Lymphocytes (e.g., a total of 80×10$^6$, 100×10$^6$, 120×10$^6$) are then added to each flask. This is considered day 0 of the CTL culture process. Cultures are not disturbed after this stimulation for 7 days.

In the second stimulation enrichment and subsequent expansion of COVID-19 specific CTLs occurs. Seven days after the initial sensitization, CTLs are re-stimulated as part of an enrichment step which helps to select for peptide specific CTL and reduces the content of other non-specific 'bystander' lymphocytes or other immune cells from the donor. Enrichment is based on preferential adherence of peptide specific CTLs to a monocyte layer which has been pulsed with the peptides used for the initial sensitization. CTLs recognizing any of the peptides as presented by the appropriate HLA allele will preferentially adhere to the monocyte plus peptide layer through creation of an immunologic synapse in contrast to 'bystander' lymphocytes, which can be gently washed away. While some 'bystander' lymphocytes may non-specifically adhere, this typically allows for an approximately 10-fold or greater enrichment of peptide-specific CTLs versus the starting material. To perform this enrichment step, monocytes (e.g., 10×10$^6$) are added to tissue culture plates. Peptides are added (e.g., at a final concentration of 2 microgram/ml each) and allowed to incubate with the monocytes (e.g., for about 90 minutes). Lymphocytes (e.g., 60×10$^6$, 70×10$^6$, 80×10$^6$, 90×10$^6$, 100×10$^6$, 110×10$^6$, or 120×10$^6$, typically the contents of one of the 75 cm$^2$ tissue culture flasks) are then added to the wells. 'Bystander' lymphocytes are removed from the wells by gentle washing with PBS after an appropriate length of time (e.g., about 5, 7.5, 10, or 12 minutes). Adherent lymphocytes are allowed to remain in contact with peptide pulsed monocytes overnight to complete the activation/restimulation process. The following day, lymphocytes are removed from monocyte layers. The dislodged, adherent lymphocytes are transferred to tissue culture flasks in media with recombinant human IL-2 (e.g., at a concentration of 50 U/ml). IL-2 is added over time (e.g., 50 U/ml every 48 hours). Media is changed if/when flasks show conversion to a more orange/yellow color. Cells are then cultured for a total of 7 days following the second stimulation. Enrichment on the monocyte layer as part of this second stimulation is critical and provides a true advantage over prior methods. It is believed that the enrichment on the monocyte layer is responsible for the significantly higher purity level amongst total T cells that has not been achieved prior to the present invention.

A third stimulation is then performed to further expand the COVID-19 peptide specific CTLs. The enrichment step performed as part of the second stimulation is not typically repeated as part of the third stimulation. However, if assessment of the percentage of COVID reactive lymphocytes (as measured by intracellular cytokine assay or tetramer assay) is below a certain limit (e.g., about 12-18%, 12%, 13%, 14%, 15%, 16%, 17% or 18%) within a day of the planned third stimulation, the procedure for the second stimulation may be repeated in lieu of the usual procedure for the third stimulation. Of the entire CTL production process, the enrichment step involves the most manipulation and is the point most vulnerable to introduce contamination and it is thus desirable to avoid repeating this more than once to the extent this is feasible. Further enrichment of percentage of COVID-19 peptide-specific CTLs is anticipated after the third stimulation, even without repeating the enrichment step. This reflects the fact that stimulated cells will grow in IL-2 containing media where unstimulated 'bystander' cells will not and that, over time, unstimulated 'bystander' cells will die off in culture leading to a more enriched product. By setting the above threshold for when the enrichment step from the second stimulation may be repeated, it is anticipated that it will be repeated infrequently, and only when essential to the manufacturing process.

After seven days of culture in the tissue culture flask (day 14 of CTL stimulation/culture overall), cells are counted and restimulated with monocytes and peptide in G-Rex flasks. The lymphocyte:monocyte ratio may be between 4:1 and 5:1, 4:1, 4.1:1, 4.2:1, 4.3:1, 4.4:1, 4.5:1, 4.6:1, 4.7:1, 4.8:1, 4.9:1, or 5:1. Each peptide is again added at a concentration of 2 microgram/ml. Lymphocytes ($15 \times 10^6$) are added to each G-Rex10 flask for this secondary restimulation. Sensitization is performed in media (e.g., 40 ml of complete media) with IL-2 (e.g., 50 U/ml).

Following the third stimulation, CTLs are again cultured (e.g., for 7 days). Media and IL-2 change may be performed every 3-4 days depending on when media color change is observed.

Following conclusion of this 21 day period of stimulation and expansion, CTLs will be assessed as to whether they meet the necessary criteria and, if so, harvested for cryopreservation (e.g., within 24 hours thereafter). Optionally, in some circumstances a fourth stimulation may be performed following the guidelines for the third stimulation. This will typically be performed when further cell expansion is deemed desirable to increase the number of doses of CTLs being generated or if products fall slightly short of release criteria and it is thought that an additional round of stimulation/expansion will allow the product to meet all criteria. Restimulation steps may be performed at 6-10 day intervals (e.g., 6 day, 7 day, 8 day, 9, day, 10 day intervals), though these steps may occur up to one day earlier or later than this typical 7-day interval, if necessary.

After completion of the three in vitro stimulation-expansion cycles products are then screened for appropriate cellular content, function, viability and sterility.

Appropriate cellular content means at least 20% (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%) of the cells will respond to COVID-19 peptides based on intracellular cytokine (ICC) staining, or tetrameter binding, and that the content of naïve T cells, monocytes, and NK cells in the product is less than 2.5% (e.g., about 2.4%, about 2.3%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, or about 0.1%).

Function is based on about 40% cytolytic activity of the CTL toward peptide pulsed targets at an effector:target ratio of 40:1.

Viability should exceed 70%, for example viability of 75%, 80%, 85%, 90%, 95%, or 99% may be appropriate.

Sterility may be assessed through routine and fungal cultures, as well as assays for *mycoplasma* and endotoxin. CTLs may be cryopreserved in cryobags at any desired concentration, for example a concentration of about $2 \times 10^6$ per milliliter, and stored for later use in the methods disclosed herein.

Pharmaceutical Compositions Containing COVID-19 Peptide-Specific Cytotoxic T Cells (CTLs)

In one aspect, the invention relates to pharmaceutical compositions for intravenous delivery that contain COVID-19 peptide specific CTLs. The pharmaceutical compositions are for intravenous delivery to an individual in need thereof, for example, by infusion through a peripheral IV, central line or mid line catheter. The pharmaceutical compositions typically also include one or more carriers or excipients that are suitable for delivery of cryopreserved CTLs, such as DMSO and the like.

In one embodiment, the pharmaceutical composition comprises COVID-19 specific CTLs that have been sensitized against COVID-19 peptides binding to specific HLA-A1 alleles (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, or a combination thereof).

In one embodiment, the pharmaceutical composition comprises COVID-19 specific CTLs that have been sensitized against COVID-19 peptides binding to specific HLA-A2 alleles (e.g., SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, or a combination thereof).

In one embodiment, the pharmaceutical composition comprises COVID-19 specific CTLs that have been sensitized against COVID-19 peptides binding to specific HLA-B7 alleles (e.g., SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, or a combination thereof).

In one embodiment, the pharmaceutical composition comprises COVID-19 specific CTLs that have been sensitized against COVID-19 peptides binding to specific HLA-B40 alleles (e.g., SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, or a combination thereof).

In one embodiment, the pharmaceutical composition comprises COVID-19 specific CTLs that have been sensitized against COVID-19 peptides binding to specific HLA-Cw7 alleles (e.g., SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, or a combination thereof).

In one embodiment, the pharmaceutical composition comprises COVID-19 specific CTLs that have been sensitized against one or more COVID-19 peptides binding to any one or combination of HLA-A1, A2, B7, B40, Cw7 alleles. In another embodiment, the pharmaceutical composition comprises COVID-19 specific CTLs that have been sensitized against a combination of COVID-19 peptides binding to a combination of alleles (e.g, a half dose of A2 CTL combined with a half dose of B7 CTL).

In some embodiments, the pharmaceutical composition comprises cryopreserved CTLs in DMSO, RPMI-1640, albumin, or a combination thereof.

If desired, the pharmaceutical compositions described herein can also include one or more additional anti-COVID-19 agents, such as remdesivir.

The pharmaceutical composition can be in any form that is suitable for intravenous administration.

EXEMPLIFICATION

Example 1: Pretreatment Period/Screening

Patients with a documented diagnosis of COVID-19 will have their blood tested for rapid, low resolution human leukocyte antigens (HLA) typing with high resolution PCR SSP supplementation if they have a potentially appropriate HLA antigen for the study (HLA-A1, A2, B7, B40, Cw7). The high-resolution supplementation will ensure that they are HLA-A*01:01, A*02:01, B*07:02, B*40:01, C*07:02 and thus match the CTL for one or more alleles.

If a patient meets eligibility criteria for the study based on age or comorbid condition (s) and they possess at least 1 HLA allele in common with a cryopreserved CTL product, they will receive COVID-19 specific CTLs. Blood for high resolution typing confirmation will be collected and analyzed. Due to the seriousness of a COVID-19 infection, CTL therapy will not be withheld while awaiting the results of central high-resolution confirmatory HLA typing. Patients who do not possess HLA alleles in common with the cryopreserved CTLs will serve as a contemporaneous COVID-19 comparison group.

Example 2: Peptide Preparation

COVID-19 peptides binding to specific HLA alleles are culled from the literature and added to the peptide table. Peptides are added sequentially to the table and given a lab designation that reflects the HLA allele to which it binds plus a two-digit extension after a dash. For example, A*02:01-03 refers to the third peptide on the table which binds to HLA-A*02:01. Peptides used for stimulation of CTL that will be used clinically are purchased from CS Bio or a similar vendor capable of making in vivo grade material.

TABLE 1

| HLA-A*02:01 | |
|---|---|
| Peptide Number | Peptide Amino Acid Sequence |
| 01 | ILLNKHIDA* (SEQ ID NO: 1) |
| 02 | GMSRIGMEV (SEQ ID NO: 2) |

TABLE 1-continued

| HLA-A*02:01 | |
|---|---|
| Peptide Number | Peptide Amino Acid Sequence |
| 03 | ALNTPKDHI (SEQ ID NO: 3) |
| 04 | LALLLLDRL (SEQ ID NO: 4) |
| 05 | LLLDRLNQL (SEQ ID NO: 5) |
| 06 | LQLPQGTTL (SEQ ID NO: 6) |
| 07 | FIAGLIAIV (SEQ ID NO: 7) |
| 08 | ALNTLVKQL (SEQ ID NO: 8) |
| 09 | LITGRLQSL (SEQ ID NO: 9) |
| 10 | NLNESLIDL (SEQ ID NO: 10) |
| 11 | RLNEVAKNL (SEQ ID NO: 11 |
| 12 | VLNDILSRL (SEQ ID NO: 12) |
| 13 | VVFLHVTYV (SEQ ID NO: 13) |
| 14 | ALSKGVHFV (SEQ ID NO: 14) |
| 15 | VLAWLYAAV (SEQ ID NO: 15) |
| 16 | KLWAQCVQL (SEQ ID NO: 16) |
| 17 | YLQPRTFLL (SEQ ID NO: 17) |
| 18 | LLYDANYF (SEQ ID NO: 18) |
| 19 | ALWEIQQVV (SEQ ID NO: 19) |
| 20 | YLFDESGEFK (SEQ ID NO: 20) |
| 21 | FLLNKEMYL (SEQ ID NO: 21) |
| 22 | FLLPSLATV (SEQ ID NO: 22) |
| 23 | FLAFVVFLL (SEQ ID NO: 23) |
| 24 | KLLEQWNLV (SEQ ID NO: 24) |
| 25 | SIWNLDYIINL (SEQ ID NO: 25) |
| 26 | IFLALITL (SEQ ID NO: 26) |
| 27 | FLVFLGIITTV (SEQ ID NO: 27) |

TABLE 2

| HLA-A*01:01 | |
|---|---|
| Peptide Number | Peptide Amino Acid Sequence |
| 01 | TTDPSFLGRY (SEQ ID NO: 28) |
| 02 | LTDEMIAQY (SEQ ID NO: 29) |
| 03 | PTDNYITTTY (SEQ ID NO: 30) |
| 04 | FTSDYYQLY (SEQ ID NO: 31) |
| 05 | ATSRTLSYY (SEQ ID NO: 32) |
| 06 | CTDDNALAYY (SEQ ID NO: 33) |
| 07 | DTDFVNEFY (SEQ ID NO: 34) |
| 08 | NTCDGTTFTY (SEQ ID NO: 35) |
| 09 | GTDLEGNFY (SEQ ID NO: 36) |
| 10 | RTFKVSIWNLDY (SEQ ID NO: 37) |
| 11 | ISEHDYQIGGY (SEQ ID NO: 38) |
| 12 | AGDSGFAAY (SEQ ID NO: 39) |
| 13 | RQEEVQELY (SEQ ID NO: 40) |
| 14 | VDEAGSKSPIQY (SEQ ID NO: 41) |
| 15 | SPDDQIGYY (SEQ ID NO: 42) |
| 16 | GTGPEAGLPY (SEQ ID NO: 43) |
| 17 | LIDLQELGKY (SEQ ID NO: 44) |

TABLE 3

| HLA-B*07:02 | |
|---|---|
| Peptide Number | Peptide Amino Acid Sequence |
| 01 | SPRWYFYYL (SEQ ID NO: 45) |
| 02 | RPDTRYVL (SEQ ID NO: 46) |
| 03 | IPRRNVATL (SEQ ID NO: 47) |
| 04 | APHGHVMVEL (SEQ ID NO: 48) |
| 05 | TPINLVRDL (SEQ ID NO: 49) |
| 06 | APFLYLYAL (SEQ ID NO: 50) |
| 07 | KPSFYVYSRV (SEQ ID NO: 51) |
| 08 | RPLLESELVI (SEQ ID NO: 52) |
| 09 | HPLADNKFAL (SEQ ID NO: 53) |
| 10 | EPKLGSLVV (SEQ ID NO: 54) |
| 11 | FPRGQGVPI (SEQ ID NO: 55) |
| 12 | FPFTIYSLLL (SEQ ID NO: 56) |
| 13 | NPANNAAIVL (SEQ ID NO: 57) |

TABLE 4

HLA-B*40:01

| Peptide Number | Peptide Amino Acid Sequence |
| --- | --- |
| 01 | SELVIGAVIL (SEQ ID NO: 58) |
| 02 | MEVTPSGTWL (SEQ ID NO: 59) |
| 03 | IEYPIIGDEL (SEQ ID NO: 60) |
| 04 | AEIVDTVSAL (SEQ ID NO: 61) |
| 05 | SEPVLKGVKL (SEQ ID NO: 62) |
| 06 | YEGNSPFHPL (SEQ ID NO: 63) |
| 07 | LEYHDVRVVL (SEQ ID NO: 64) |
| 08 | NESLIDLQEL (SEQ ID NO: 65) |
| 09 | TEAFEKMVSL (SEQ ID NO: 66) |
| 10 | TEVPANSTVL (SEQ ID NO: 67) |

TABLE 5

HLA-C*07:02

| Peptide Number | Peptide Amino Acid Sequence |
| --- | --- |
| 01 | NYMPYFFTL (SEQ ID NO: 68) |
| 02 | VRFPNITNL (SEQ ID NO: 69) |
| 03 | YYQLYSTQL (SEQ ID NO: 70) |
| 04 | NRFLYIIKL (SEQ ID NO: 71) |
| 05 | IRQEEVQEL (SEQ ID NO: 72) |
| 06 | EYHDVRVVL (SEQ ID NO: 73) |
| 07 | QRNAPRITF (SEQ ID NO: 74) |
| 08 | KKADETQAL (SEQ ID NO: 75) |
| 09 | VYDPLQPEL (SEQ ID NO: 76) |
| 10 | IYNDKVAGF (SEQ ID NO: 77) |

Example 3: Dendritic Cell Preparation from Monocytes

Dendritic cells are prepared to aid in the generation of specific cytotoxic T lymphocytes (CTLs). We begin typically with $1 \times 10^7$ monocytes or multiples thereof. After centrifuging, decant the supernatant and resuspend in complete media (RPMI 1640 supplemented with 10% heat inactivated normal AB serum) along with DNase. Check and record cell count and viability by trypan blue. Transfer to a 6 well plate, then incubate at 37° C., followed by a wash. Add complete media which has been supplemented with GM-CSF and IL-4. The day on which monocytes begin culture in GM-CSF and IL-4 is referred to as Day +1 of the procedure. On the next day (Day +2) add four maturation cytokines IL-6, IL-1 beta, TNF alpha, PGE2. Final concentrations of maturation cytokines vary, but in one case are as follows:

| | |
| --- | --- |
| IL-6 | 1000 IU/ml |
| PGE2 | 1 microgram/ml |
| IL-1 beta | 10 ng/ml |
| TNF alpha | 10 ng/ml |

Place the 6-well plate back in the incubator at 37° C. On Day +3, transfer the dendritic cells to a conical tube, centrifuge, decant the supernatant, and resuspend in complete media to which the peptides have been added at a concentration of 2 microgram/ml of each peptide, then incubate. At this point, the dendritic cells are ready for co-culture with lymphocytes. As monocytes mature into dendritic cells, they undergo changes in shape and detach. Approximately half the number of dendritic cells are recovered compared to the starting number of monocytes.

Example 4: Dendritic Cell Co-Culture with Lymphocytes

Dendritic cells prepared in Example 3 are resuspended in complete media with peptides at a cell concentration of $1 \times 10^6$ /ml with peptides at a concentration of 2 microgram/ml each. While the dendritic cells are pulsed with peptide, prepare the lymphocytes. Thaw 100 million lymphocytes. Perform cell count and viability tests with trypan blue. The goal is a lymphocyte:monocyte (DC) ratio of 20:1 (100 million: 5 million). Lymphocyte viability should be greater than 95%. After centrifugation, resuspend the thawed lymphocytes in complete media with penicillin/streptomycin and transfer to a culture flask, then incubate. After the dendritic cells have been incubated with peptide remove from the incubator, centrifuge again, then resuspend in complete media with penicillin/streptomycin. Add the dendritic cell suspension to a flask which contains the lymphocytes. Incubate the mixture, then add additional complete media with penicillin/streptomycin. After 7 days of co-culture (range 6-8) cells are ready for analysis and re-stimulation.

Example 5: Stimulation & Enrichment on a Monocyte Monolayer

This procedure is for enrichment of T cells responding to specific peptides on a monocyte monolayer. The T cells can be enriched, activated, and expanded in culture. Beginning with $10 \times 10^6$ monocytes, verify cell count and assess viability. Viability should be 92% or higher. Resuspend the monocytes along with DNase in complete media. Incubate, then carefully remove the media. Rinse the monocyte membrane with PBS and subsequently transfer the PBS out of the well. After the PBS is removed, add complete media containing peptides (with each peptide at a 2 microgram/ml concentration) and incubate (during this incubation prepare the lymphocytes). After the incubation the unbound peptides are removed. Peptides are removed as follows: remove the media as described and then wash with PBS.

Harvest the lymphocytes in culture (being careful to gently agitate the flask to get any lymphocytes from the bottom), centrifuge, decant the supernatant and resuspend in complete media and perform a cell count and viability test. Place back in the incubator.

After washing the monocytes, the activated lymphocytes that were transferred into complete media are gently added to the well containing the monocytes and placed in the incubator. Placing the plate in the incubator is the start of T cell selection. Once placed in the incubator, do not disturb the cells in any way during selection.

The selection time to be used is based on the number of lymphocytes undergoing the selection process. If there are less than 90 million lymphocytes, the selection time will be ten minutes. If there are 90 million or more lymphocytes, the selection time will be 7.5 minutes. Once the timer goes off the selection time is complete, and the cells are removed from the incubator.

Remove the media containing the non-adherent cells. After the media is removed, wash with PBS as described above. As before, it is critical to be gentle at this point, as the lymphocytes are adherent to the monocytes and, as the monocytes start to die, the lymphocytes become looser. After the third wash you should notice a white film on the bottom of the plate. This is a good sign (evidence of lymphocytes adhering to the monocytes), and it may be so opaque that one cannot see through the bottom. Exercise caution so as not to let the cells dry out.

Add complete media with penicillin/strep, and place in the incubator. Remove the plate from the incubator and look at the well under the microscope. If you see excessive floating cells remove the media and wash once again with warm PBS. If few or no floating cells observed, incubate overnight. After the fourth wash (if needed), add complete media with pen/strep and incubate overnight.

T Cell Expansion

The next day using a transfer pipette, transfer all of the cells remaining in the plate to a tissue culture flask containing complete media with pen/strep containing IL-2. Every 2 days IL-2 should be added to the cultures Example 6: Stimulation with Monocytes in Flasks This procedure stimulates lymphocytes with monocytes that have been pulsed with peptide in the absence of a T cell enrichment/selection step (such as utilized in Example 5).

Typically, 10 million monocytes are required. Although the ratio of lymphocytes to monocytes may vary somewhat based on available monocytes and the pace of lymphocyte growth after prior stimulations, the ratio will typically be close to 5:1. DNase should be added to the media.

After counting and checking viability, re-suspend the monocytes in complete media containing DNase and to which peptides have been added at a concentration of 2 micrograms/ml for each peptide. The cells should be resuspended in a conical tube. Vortex briefly and place the tube in an incubator. Incubate, centrifuge, then decant the supernatant. Add complete media and vortex to re-suspend. While the monocytes are being pulsed with peptides, the lymphocytes to be stimulated with the monocytes should be counted and viability checked. Re-suspend the lymphocytes in complete media and place in a tissue culture flask. Add the monocytes to the lymphocytes, and then incubate.

Following the above incubation of monocytes and lymphocytes, add complete media with pen/strep containing IL-2. Return the flasks to the incubator. IL-2 should be added to the cultures every two days.

Example 7: Intracellular Cytokine (ICC) Assay

This procedure is for performing ICC cell preparation prior to staining and performing flow cytometry. Prepare the monocytes before working with the lymphocytes. Thaw monocytes as described in the cell thawing SOP. Count cells and check viability by Trypan Blue. Monocytes must be primed with peptide(s) before the lymphocytes are added (except for the negative control). Always include a negative control in parallel which is monocytes not primed with any peptide.

Re-suspend 0.5 million monocytes in 2 ml of 37 degree complete media in a 5 or 10 ml tube. Add the peptide (for negative control no peptide). The final concentration of each peptide is 2 microgram/ml. If multiple peptides are added to a tube, each should be present at a concentration of 2 microgram/ml. Incubate at 37,° C. for 90 minutes to "prime the monocytes". This is done at 37° C. with the 5 or 10 cc tube lying on its side with the cap loosened and the tube balanced on the top of a 6 well plate. After 90 minutes centrifuge at 10 minutes 482 g at room temperature. Decant the supernatant being careful not to decant the monocytes nor to let them dry out after decanting. Add 2 million lymphocytes to each tube (see below for lymphocyte preparation). The ratio of lymphocytes to monocytes is in this example is 4:1 which is appropriate when the frequency of peptide specific lymphocytes is low (below 20%) as would be the case after an initial peptide priming. As the frequency of peptide reactive cells in the lymphocyte population rises with sequential priming, this ratio should decrease. For example, when peptide specific T cells approach purities above 80%, lymphocyte:monocyte ratios should approach 1:1.

Lymphocyte preparation: Typically, this is started after pulsing the monocytes with peptide and initiating the 90 minute incubation with peptide. Count each "lymphocyte culture". Two million lymphocytes are required for each ICC experiment ("reaction") Aliquot the appropriate volume for 2 million lymphocytes and centrifuge at 10 minutes at 482 g at room temperature. Decant and resuspend in 2 ml of 37° C. CM. After decanting the supernatant from the monocytes (above), add these 2 ml to the monocyte tubes. Make sure all the cells are mixed by gentle vortex. Incubate for 2 hours at 37° C. in a 5 or 10 cc tube on its side balanced on the top of a 6 well plate with the cap loosened. At the end of 2 hours, add brefeldin A and incubate for 37 degrees for 4 hours.

Stain for ICC. The number of cells reactive with peptide will be very low (1% or less in some cases after initial sensitization), but should rise to much higher levels with repeated stimulation.

Example 8: Manufacture of 3$^{rd}$ Party COVID-19 Specific CTLs

Lymphocytes will be exposed to a limited number (up to 20) of peptides known to bind to the HLA restriction element of interest. Lymphocytes are initially stimulated with peptide pulsed dendritic cells and twice more with peptide pulsed monocytes. As part of the first monocyte-peptide re-stimulation, CTL of interest are enriched due to their preferential adherence to a monocyte-peptide monolayer. The highest frequencies of viral reactive lymphocytes we have seen reported in the literature are less than 2%, (Leen et al., 2006) while our release criteria require at least 20% viral reactive CTLs. Products will be produced by the Jefferson Cell processing laboratory in Philadelphia. Release criteria are as follows: (1) the products must demonstrate that at least 20% of the CTL react to COVID-19 peptides in the ICC assay. (Note that reactivity to peptides is always higher in tetramer assays than in ICC assay, and thus the latter is a more rigorous measure.) (2) 40% lysis of appropriate target cells at a 20:1 Effector:Target ratio (3) flow cytometry must reveal that the cell product contains ≤2.5% monocytes, ≤2.5% NK cells, ≤2.5% naïve T cells. These latter populations were thought to be of concern in triggering GVHD in the BMT studies. While we do not believe they are relevant for the COVID-19 population, we include them in our release criteria until more data is available regarding safety.

FIG. 1 shows the expansion of COVID-19 CTLs through the application of the proposed laboratory processes. The graphs illustrate the background level (left panel), the detection of a small population of CD8+ T cells after the first week of in vitro culture and enrichment to 15% (right panel) after selection and further expansion. The x-axis reflects staining with the CD8 marker identifying the cytotoxic subset of T cells. The y-axis reflects gamma interferon production in response to stimulation with COVID-19 peptides capable of binding to HLA-A*02:01. We expect further enrichment will consistently occur with the subsequent stimulation/expansion steps in our process.

The entire teachings of all documents cited herein are hereby incorporated herein by reference.

What is claimed is:

1. A pharmaceutical composition comprising cells comprising COVID-19 peptide specific cytotoxic T lymphocytes (CTLs) that are specifically enriched cells reactive to COVID-19 peptides, wherein said CTLs are sensitized against multiple peptides restricted against a single HLA allele by in vitro stimulation, wherein at least 20% of said CTLs are reactive to COVID-19 peptides, and wherein said cells comprise less than 2.5% of naïve T cells, monocytes, NK cells, or any combination thereof.

2. The pharmaceutical composition of claim 1, wherein said CTLs are from multiple donors.

3. The pharmaceutical composition of claim 1, wherein the CTLs have been sensitized against one or more COVID-19 peptides binding to specific HLA-A 1 alleles selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and a combination thereof.

4. The pharmaceutical composition of claim 1, wherein the CTLs have been sensitized against one or more COVID-19 peptides binding to specific HLA-A2 alleles selected from the group consisting of SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and a combination thereof.

5. The pharmaceutical composition of claim 1, wherein the CTLs have been sensitized against one or more COVID-19 peptides binding to specific HLA-B7 alleles selected from the group consisting of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, and a combination thereof.

6. The pharmaceutical composition of claim 1, wherein the CTLs have been sensitized against one or more COVID-19 peptides binding to specific HLA-B40 alleles selected from the group consisting of SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, and a combination thereof.

7. The pharmaceutical composition of claim 1, wherein the CTLs have been sensitized against one or more COVID-19 peptides binding to specific HLA-Cw7 alleles selected from the group consisting of SEQ ID NO:68, SEQ ID NO:69, SEQ ID NO:70, SEQ ID NO:71, SEQ ID NO:72, SEQ ID NO:73, SEQ ID NO:7 4, SEQ ID NO:75, SEQ ID NO:76, SEQ ID NO:77, and a combination thereof.

8. The pharmaceutical composition of claim 1, wherein the CTLs have been sensitized against one or more COVID-19 peptides binding to any one or a combination of HLA-A1, A2, B7, B40, or Cw7 alleles.

9. The pharmaceutical composition of claim 1, wherein the pharmaceutical composition comprises cryopreserved CTLs in DMSO, RPMI-1640, albumin, or a combination thereof.

10. The pharmaceutical composition of claim 1, wherein the pharmaceutical composition comprises one or more additional anti-COVID-19 agents.

11. The pharmaceutical composition of claim 1, wherein the pharmaceutical composition is in a form that is suitable for intravenous administration.

* * * * *

SEQUENCE LISTING

<160> NUMBER OF SEQ ID NOS: 77

<210> SEQ ID NO 1
<211> LENGTH: 9
<212> TYPE: PRT
<213> ORGANISM: Severe acute respiratory syndrome coronavirus 2

<400> SEQUENCE: 1

Ile Leu Leu Asn Lys His Ile Asp Ala
1               5

<210> SEQ ID NO 2
<211> LENGTH: 9
<212> TYPE: PRT
<213> ORGANISM: Severe acute respiratory syndrome coronavirus 2

<400> SEQUENCE: 2

Gly Met Ser Arg Ile Gly Met Glu Val
1               5

<210> SEQ ID NO 3
<211> LENGTH: 9
<212> TYPE: PRT
<213> ORGANISM: Severe acute respiratory syndrome coronavirus 2

<400> SEQUENCE: 3

Ala Leu Asn Thr Pro Lys Asp His Ile
1               5

<210> SEQ ID NO 4
<211> LENGTH: 9
<212> TYPE: PRT
<213> ORGANISM: Severe acute respiratory syndrome coronavirus 2

<400> SEQUENCE: 4

Leu Ala Leu Leu Leu Leu Asp Arg Leu
1               5

<210> SEQ ID NO 5
<211> LENGTH: 9
<212> TYPE: PRT
<213> ORGANISM: Severe acute respiratory syndrome coronavirus 2

<400> SEQUENCE: 5

Leu Leu Leu Asp Arg Leu Asn Gln Leu
1               5

<210> SEQ ID NO 6
<211> LENGTH: 9
<212> TYPE: PRT
<213> ORGANISM: Severe acute respiratory syndrome coronavirus 2

<400> SEQUENCE: 6

Leu Gln Leu Pro Gln Gly Thr Thr Leu
1               5

<210> SEQ ID NO 7
<211> LENGTH: 9
<212> TYPE: PRT
<213> ORGANISM: Severe acute respiratory syndrome coronavirus 2

<400> SEQUENCE: 7

Phe Ile Ala Gly Leu Ile Ala Ile Val
1               5

```
<210> SEQ ID NO 8
<211> LENGTH: 9
<212> TYPE: PRT
<213> ORGANISM: Severe acute respiratory syndrome coronavirus 2

<400> SEQUENCE: 8

Ala Leu Asn Thr Leu Val Lys Gln Leu
1               5

<210> SEQ ID NO 9
<211> LENGTH: 9
<212> TYPE: PRT
<213> ORGANISM: Severe acute respiratory syndrome coronavirus 2

<400> SEQUENCE: 9

Leu Ile Thr Gly Arg Leu Gln Ser Leu
1               5

<210> SEQ ID NO 10
<211> LENGTH: 9
<212> TYPE: PRT
<213> ORGANISM: Severe acute respiratory syndrome coronavirus 2

<400> SEQUENCE: 10

Asn Leu Asn Glu Ser Leu Ile Asp Leu
1               5

<210> SEQ ID NO 11
<211> LENGTH: 9
<212> TYPE: PRT
<213> ORGANISM: Severe acute respiratory syndrome coronavirus 2

<400> SEQUENCE: 11

Arg Leu Asn Glu Val Ala Lys Asn Leu
1               5

<210> SEQ ID NO 12
<211> LENGTH: 9
<212> TYPE: PRT
<213> ORGANISM: Severe acute respiratory syndrome coronavirus 2

<400> SEQUENCE: 12

Val Leu Asn Asp Ile Leu Ser Arg Leu
1               5

<210> SEQ ID NO 13
<211> LENGTH: 9
<212> TYPE: PRT
<213> ORGANISM: Severe acute respiratory syndrome coronavirus 2

<400> SEQUENCE: 13

Val Val Phe Leu His Val Thr Tyr Val
1               5

<210> SEQ ID NO 14
<211> LENGTH: 9
<212> TYPE: PRT
<213> ORGANISM: Severe acute respiratory syndrome coronavirus 2

<400> SEQUENCE: 14

Ala Leu Ser Lys Gly Val His Phe Val
1               5
```

<210> SEQ ID NO 15
<211> LENGTH: 9
<212> TYPE: PRT
<213> ORGANISM: Severe acute respiratory syndrome coronavirus 2

<400> SEQUENCE: 15

Val Leu Ala Trp Leu Tyr Ala Ala Val
1               5

<210> SEQ ID NO 16
<211> LENGTH: 9
<212> TYPE: PRT
<213> ORGANISM: Severe acute respiratory syndrome coronavirus 2

<400> SEQUENCE: 16

Lys Leu Trp Ala Gln Cys Val Gln Leu
1               5

<210> SEQ ID NO 17
<211> LENGTH: 9
<212> TYPE: PRT
<213> ORGANISM: Severe acute respiratory syndrome coronavirus 2

<400> SEQUENCE: 17

Tyr Leu Gln Pro Arg Thr Phe Leu Leu
1               5

<210> SEQ ID NO 18
<211> LENGTH: 8
<212> TYPE: PRT
<213> ORGANISM: Severe acute respiratory syndrome coronavirus 2

<400> SEQUENCE: 18

Leu Leu Tyr Asp Ala Asn Tyr Phe
1               5

<210> SEQ ID NO 19
<211> LENGTH: 9
<212> TYPE: PRT
<213> ORGANISM: Severe acute respiratory syndrome coronavirus 2

<400> SEQUENCE: 19

Ala Leu Trp Glu Ile Gln Gln Val Val
1               5

<210> SEQ ID NO 20
<211> LENGTH: 10
<212> TYPE: PRT
<213> ORGANISM: Severe acute respiratory syndrome coronavirus 2

<400> SEQUENCE: 20

Tyr Leu Phe Asp Glu Ser Gly Glu Phe Lys
1               5                   10

<210> SEQ ID NO 21
<211> LENGTH: 9
<212> TYPE: PRT
<213> ORGANISM: Severe acute respiratory syndrome coronavirus 2

<400> SEQUENCE: 21

Phe Leu Leu Asn Lys Glu Met Tyr Leu
1               5

```
<210> SEQ ID NO 22
<211> LENGTH: 9
<212> TYPE: PRT
<213> ORGANISM: Severe acute respiratory syndrome coronavirus 2

<400> SEQUENCE: 22

Phe Leu Leu Pro Ser Leu Ala Thr Val
1               5

<210> SEQ ID NO 23
<211> LENGTH: 9
<212> TYPE: PRT
<213> ORGANISM: Severe acute respiratory syndrome coronavirus 2

<400> SEQUENCE: 23

Phe Leu Ala Phe Val Val Phe Leu Leu
1               5

<210> SEQ ID NO 24
<211> LENGTH: 9
<212> TYPE: PRT
<213> ORGANISM: Severe acute respiratory syndrome coronavirus 2

<400> SEQUENCE: 24

Lys Leu Leu Glu Gln Trp Asn Leu Val
1               5

<210> SEQ ID NO 25
<211> LENGTH: 11
<212> TYPE: PRT
<213> ORGANISM: Severe acute respiratory syndrome coronavirus 2

<400> SEQUENCE: 25

Ser Ile Trp Asn Leu Asp Tyr Ile Ile Asn Leu
1               5                   10

<210> SEQ ID NO 26
<211> LENGTH: 8
<212> TYPE: PRT
<213> ORGANISM: Severe acute respiratory syndrome coronavirus 2

<400> SEQUENCE: 26

Ile Phe Leu Ala Leu Ile Thr Leu
1               5

<210> SEQ ID NO 27
<211> LENGTH: 11
<212> TYPE: PRT
<213> ORGANISM: Severe acute respiratory syndrome coronavirus 2

<400> SEQUENCE: 27

Phe Leu Val Phe Leu Gly Ile Ile Thr Thr Val
1               5                   10

<210> SEQ ID NO 28
<211> LENGTH: 10
<212> TYPE: PRT
<213> ORGANISM: Severe acute respiratory syndrome coronavirus 2

<400> SEQUENCE: 28

Thr Thr Asp Pro Ser Phe Leu Gly Arg Tyr
1               5                   10

<210> SEQ ID NO 29
<211> LENGTH: 9
```

-continued

```
<212> TYPE: PRT
<213> ORGANISM: Severe acute respiratory syndrome coronavirus 2

<400> SEQUENCE: 29

Leu Thr Asp Glu Met Ile Ala Gln Tyr
1               5

<210> SEQ ID NO 30
<211> LENGTH: 10
<212> TYPE: PRT
<213> ORGANISM: Severe acute respiratory syndrome coronavirus 2

<400> SEQUENCE: 30

Pro Thr Asp Asn Tyr Ile Thr Thr Thr Tyr
1               5                   10

<210> SEQ ID NO 31
<211> LENGTH: 9
<212> TYPE: PRT
<213> ORGANISM: Severe acute respiratory syndrome coronavirus 2

<400> SEQUENCE: 31

Phe Thr Ser Asp Tyr Tyr Gln Leu Tyr
1               5

<210> SEQ ID NO 32
<211> LENGTH: 9
<212> TYPE: PRT
<213> ORGANISM: Severe acute respiratory syndrome coronavirus 2

<400> SEQUENCE: 32

Ala Thr Ser Arg Thr Leu Ser Tyr Tyr
1               5

<210> SEQ ID NO 33
<211> LENGTH: 10
<212> TYPE: PRT
<213> ORGANISM: Severe acute respiratory syndrome coronavirus 2

<400> SEQUENCE: 33

Cys Thr Asp Asp Asn Ala Leu Ala Tyr Tyr
1               5                   10

<210> SEQ ID NO 34
<211> LENGTH: 9
<212> TYPE: PRT
<213> ORGANISM: Severe acute respiratory syndrome coronavirus 2

<400> SEQUENCE: 34

Asp Thr Asp Phe Val Asn Glu Phe Tyr
1               5

<210> SEQ ID NO 35
<211> LENGTH: 10
<212> TYPE: PRT
<213> ORGANISM: Severe acute respiratory syndrome coronavirus 2

<400> SEQUENCE: 35

Asn Thr Cys Asp Gly Thr Thr Phe Thr Tyr
1               5                   10

<210> SEQ ID NO 36
<211> LENGTH: 9
<212> TYPE: PRT
<213> ORGANISM: Severe acute respiratory syndrome coronavirus 2
```

<400> SEQUENCE: 36

Gly Thr Asp Leu Glu Gly Asn Phe Tyr
1               5

<210> SEQ ID NO 37
<211> LENGTH: 12
<212> TYPE: PRT
<213> ORGANISM: Severe acute respiratory syndrome coronavirus 2

<400> SEQUENCE: 37

Arg Thr Phe Lys Val Ser Ile Trp Asn Leu Asp Tyr
1               5                   10

<210> SEQ ID NO 38
<211> LENGTH: 11
<212> TYPE: PRT
<213> ORGANISM: Severe acute respiratory syndrome coronavirus 2

<400> SEQUENCE: 38

Ile Ser Glu His Asp Tyr Gln Ile Gly Gly Tyr
1               5                   10

<210> SEQ ID NO 39
<211> LENGTH: 9
<212> TYPE: PRT
<213> ORGANISM: Severe acute respiratory syndrome coronavirus 2

<400> SEQUENCE: 39

Ala Gly Asp Ser Gly Phe Ala Ala Tyr
1               5

<210> SEQ ID NO 40
<211> LENGTH: 9
<212> TYPE: PRT
<213> ORGANISM: Severe acute respiratory syndrome coronavirus 2

<400> SEQUENCE: 40

Arg Gln Glu Glu Val Gln Glu Leu Tyr
1               5

<210> SEQ ID NO 41
<211> LENGTH: 12
<212> TYPE: PRT
<213> ORGANISM: Severe acute respiratory syndrome coronavirus 2

<400> SEQUENCE: 41

Val Asp Glu Ala Gly Ser Lys Ser Pro Ile Gln Tyr
1               5                   10

<210> SEQ ID NO 42
<211> LENGTH: 9
<212> TYPE: PRT
<213> ORGANISM: Severe acute respiratory syndrome coronavirus 2

<400> SEQUENCE: 42

Ser Pro Asp Asp Gln Ile Gly Tyr Tyr
1               5

<210> SEQ ID NO 43
<211> LENGTH: 10
<212> TYPE: PRT
<213> ORGANISM: Severe acute respiratory syndrome coronavirus 2

-continued

```
<400> SEQUENCE: 43

Gly Thr Gly Pro Glu Ala Gly Leu Pro Tyr
1               5                   10

<210> SEQ ID NO 44
<211> LENGTH: 10
<212> TYPE: PRT
<213> ORGANISM: Severe acute respiratory syndrome coronavirus 2

<400> SEQUENCE: 44

Leu Ile Asp Leu Gln Glu Leu Gly Lys Tyr
1               5                   10

<210> SEQ ID NO 45
<211> LENGTH: 9
<212> TYPE: PRT
<213> ORGANISM: Severe acute respiratory syndrome coronavirus 2

<400> SEQUENCE: 45

Ser Pro Arg Trp Tyr Phe Tyr Tyr Leu
1               5

<210> SEQ ID NO 46
<211> LENGTH: 8
<212> TYPE: PRT
<213> ORGANISM: Severe acute respiratory syndrome coronavirus 2

<400> SEQUENCE: 46

Arg Pro Asp Thr Arg Tyr Val Leu
1               5

<210> SEQ ID NO 47
<211> LENGTH: 9
<212> TYPE: PRT
<213> ORGANISM: Severe acute respiratory syndrome coronavirus 2

<400> SEQUENCE: 47

Ile Pro Arg Arg Asn Val Ala Thr Leu
1               5

<210> SEQ ID NO 48
<211> LENGTH: 10
<212> TYPE: PRT
<213> ORGANISM: Severe acute respiratory syndrome coronavirus 2

<400> SEQUENCE: 48

Ala Pro His Gly His Val Met Val Glu Leu
1               5                   10

<210> SEQ ID NO 49
<211> LENGTH: 9
<212> TYPE: PRT
<213> ORGANISM: Severe acute respiratory syndrome coronavirus 2

<400> SEQUENCE: 49

Thr Pro Ile Asn Leu Val Arg Asp Leu
1               5

<210> SEQ ID NO 50
<211> LENGTH: 9
<212> TYPE: PRT
<213> ORGANISM: Severe acute respiratory syndrome coronavirus 2
```

```
<400> SEQUENCE: 50

Ala Pro Phe Leu Tyr Leu Tyr Ala Leu
1               5

<210> SEQ ID NO 51
<211> LENGTH: 10
<212> TYPE: PRT
<213> ORGANISM: Severe acute respiratory syndrome coronavirus 2

<400> SEQUENCE: 51

Lys Pro Ser Phe Tyr Val Tyr Ser Arg Val
1               5                   10

<210> SEQ ID NO 52
<211> LENGTH: 10
<212> TYPE: PRT
<213> ORGANISM: Severe acute respiratory syndrome coronavirus 2

<400> SEQUENCE: 52

Arg Pro Leu Leu Glu Ser Glu Leu Val Ile
1               5                   10

<210> SEQ ID NO 53
<211> LENGTH: 10
<212> TYPE: PRT
<213> ORGANISM: Severe acute respiratory syndrome coronavirus 2

<400> SEQUENCE: 53

His Pro Leu Ala Asp Asn Lys Phe Ala Leu
1               5                   10

<210> SEQ ID NO 54
<211> LENGTH: 9
<212> TYPE: PRT
<213> ORGANISM: Severe acute respiratory syndrome coronavirus 2

<400> SEQUENCE: 54

Glu Pro Lys Leu Gly Ser Leu Val Val
1               5

<210> SEQ ID NO 55
<211> LENGTH: 9
<212> TYPE: PRT
<213> ORGANISM: Severe acute respiratory syndrome coronavirus 2

<400> SEQUENCE: 55

Phe Pro Arg Gly Gln Gly Val Pro Ile
1               5

<210> SEQ ID NO 56
<211> LENGTH: 10
<212> TYPE: PRT
<213> ORGANISM: Severe acute respiratory syndrome coronavirus 2

<400> SEQUENCE: 56

Phe Pro Phe Thr Ile Tyr Ser Leu Leu Leu
1               5                   10

<210> SEQ ID NO 57
<211> LENGTH: 10
<212> TYPE: PRT
<213> ORGANISM: Severe acute respiratory syndrome coronavirus 2
```

<400> SEQUENCE: 57

Asn Pro Ala Asn Asn Ala Ala Ile Val Leu
1               5                   10

<210> SEQ ID NO 58
<211> LENGTH: 10
<212> TYPE: PRT
<213> ORGANISM: Severe acute respiratory syndrome coronavirus 2

<400> SEQUENCE: 58

Ser Glu Leu Val Ile Gly Ala Val Ile Leu
1               5                   10

<210> SEQ ID NO 59
<211> LENGTH: 10
<212> TYPE: PRT
<213> ORGANISM: Severe acute respiratory syndrome coronavirus 2

<400> SEQUENCE: 59

Met Glu Val Thr Pro Ser Gly Thr Trp Leu
1               5                   10

<210> SEQ ID NO 60
<211> LENGTH: 10
<212> TYPE: PRT
<213> ORGANISM: Severe acute respiratory syndrome coronavirus 2

<400> SEQUENCE: 60

Ile Glu Tyr Pro Ile Ile Gly Asp Glu Leu
1               5                   10

<210> SEQ ID NO 61
<211> LENGTH: 10
<212> TYPE: PRT
<213> ORGANISM: Severe acute respiratory syndrome coronavirus 2

<400> SEQUENCE: 61

Ala Glu Ile Val Asp Thr Val Ser Ala Leu
1               5                   10

<210> SEQ ID NO 62
<211> LENGTH: 10
<212> TYPE: PRT
<213> ORGANISM: Severe acute respiratory syndrome coronavirus 2

<400> SEQUENCE: 62

Ser Glu Pro Val Leu Lys Gly Val Lys Leu
1               5                   10

<210> SEQ ID NO 63
<211> LENGTH: 10
<212> TYPE: PRT
<213> ORGANISM: Severe acute respiratory syndrome coronavirus 2

<400> SEQUENCE: 63

Tyr Glu Gly Asn Ser Pro Phe His Pro Leu
1               5                   10

<210> SEQ ID NO 64
<211> LENGTH: 10
<212> TYPE: PRT
<213> ORGANISM: Severe acute respiratory syndrome coronavirus 2

-continued

<400> SEQUENCE: 64

Leu Glu Tyr His Asp Val Arg Val Val Leu
1               5                   10

<210> SEQ ID NO 65
<211> LENGTH: 10
<212> TYPE: PRT
<213> ORGANISM: Severe acute respiratory syndrome coronavirus 2

<400> SEQUENCE: 65

Asn Glu Ser Leu Ile Asp Leu Gln Glu Leu
1               5                   10

<210> SEQ ID NO 66
<211> LENGTH: 10
<212> TYPE: PRT
<213> ORGANISM: Severe acute respiratory syndrome coronavirus 2

<400> SEQUENCE: 66

Thr Glu Ala Phe Glu Lys Met Val Ser Leu
1               5                   10

<210> SEQ ID NO 67
<211> LENGTH: 10
<212> TYPE: PRT
<213> ORGANISM: Severe acute respiratory syndrome coronavirus 2

<400> SEQUENCE: 67

Thr Glu Val Pro Ala Asn Ser Thr Val Leu
1               5                   10

<210> SEQ ID NO 68
<211> LENGTH: 9
<212> TYPE: PRT
<213> ORGANISM: Severe acute respiratory syndrome coronavirus 2

<400> SEQUENCE: 68

Asn Tyr Met Pro Tyr Phe Phe Thr Leu
1               5

<210> SEQ ID NO 69
<211> LENGTH: 9
<212> TYPE: PRT
<213> ORGANISM: Severe acute respiratory syndrome coronavirus 2

<400> SEQUENCE: 69

Val Arg Phe Pro Asn Ile Thr Asn Leu
1               5

<210> SEQ ID NO 70
<211> LENGTH: 9
<212> TYPE: PRT
<213> ORGANISM: Severe acute respiratory syndrome coronavirus 2

<400> SEQUENCE: 70

Tyr Tyr Gln Leu Tyr Ser Thr Gln Leu
1               5

<210> SEQ ID NO 71
<211> LENGTH: 9
<212> TYPE: PRT
<213> ORGANISM: Severe acute respiratory syndrome coronavirus 2

```
<400> SEQUENCE: 71

Asn Arg Phe Leu Tyr Ile Ile Lys Leu
1               5

<210> SEQ ID NO 72
<211> LENGTH: 9
<212> TYPE: PRT
<213> ORGANISM: Severe acute respiratory syndrome coronavirus 2

<400> SEQUENCE: 72

Ile Arg Gln Glu Glu Val Gln Glu Leu
1               5

<210> SEQ ID NO 73
<211> LENGTH: 9
<212> TYPE: PRT
<213> ORGANISM: Severe acute respiratory syndrome coronavirus 2

<400> SEQUENCE: 73

Glu Tyr His Asp Val Arg Val Val Leu
1               5

<210> SEQ ID NO 74
<211> LENGTH: 9
<212> TYPE: PRT
<213> ORGANISM: Severe acute respiratory syndrome coronavirus 2

<400> SEQUENCE: 74

Gln Arg Asn Ala Pro Arg Ile Thr Phe
1               5

<210> SEQ ID NO 75
<211> LENGTH: 9
<212> TYPE: PRT
<213> ORGANISM: Severe acute respiratory syndrome coronavirus 2

<400> SEQUENCE: 75

Lys Lys Ala Asp Glu Thr Gln Ala Leu
1               5

<210> SEQ ID NO 76
<211> LENGTH: 9
<212> TYPE: PRT
<213> ORGANISM: Severe acute respiratory syndrome coronavirus 2

<400> SEQUENCE: 76

Val Tyr Asp Pro Leu Gln Pro Glu Leu
1               5

<210> SEQ ID NO 77
<211> LENGTH: 9
<212> TYPE: PRT
<213> ORGANISM: Severe acute respiratory syndrome coronavirus 2

<400> SEQUENCE: 77

Ile Tyr Asn Asp Lys Val Ala Gly Phe
1               5
```

UNITED STATES PATENT AND TRADEMARK OFFICE
CERTIFICATE OF CORRECTION

| | |
|---|---|
| PATENT NO. | : 11,207,401 B1 |
| APPLICATION NO. | : 17/314154 |
| DATED | : December 28, 2021 |
| INVENTOR(S) | : Ryan Saadi |

It is certified that error appears in the above-identified patent and that said Letters Patent is hereby corrected as shown below:

In the Claims

Please correct Column 39, Line 3, Claim 3 from "HLA-A 1" to -- HLA-A2 --

Please correct Column 39, Line 15, Claim 4 from "HLA-A2" to -- HLA-A1 --

Signed and Sealed this
Fourth Day of October, 2022

Katherine Kelly Vidal
*Director of the United States Patent and Trademark Office*